United States Patent [19]

Healy et al.

[11] Patent Number: 4,520,107

[45] Date of Patent: May 28, 1985

[54] TISSUE CULTURE AND CELL GROWTH-PROMOTING MATERIAL AND ITS METHOD OF MANUFACTURE

[75] Inventors: George M. Healy, Scarborough; Kenneth D. Curry, Toronto, both of Canada

[73] Assignee: Polydex Chemicals Ltd., Nassau, The Bahamas

[21] Appl. No.: 424,862

[22] Filed: Sep. 28, 1982

[51] Int. Cl.³ ............... C12N 5/00; C12N 1/38; A61K 35/14; C07G 7/00
[52] U.S. Cl. ............... 435/240; 424/101; 260/112 B; 435/244; 435/948
[58] Field of Search ............... 435/240, 241, 948, 244; 424/101; 260/112 B

[56] References Cited

U.S. PATENT DOCUMENTS

| | | | |
|---|---|---|---|
| 1,378,896 | 5/1921 | Penfold | 424/101 |
| 1,495,364 | 5/1924 | Wescott | 424/101 |
| 1,513,949 | 11/1924 | Wescott | 424/101 |
| 2,577,353 | 12/1951 | Naidu et al. | 260/112 B |

OTHER PUBLICATIONS

Grinnell et al., "Fibroblast Adhesion to Fibrinogen and Fibrin Substrata: Requirement for Cold-Insoluble Globulin (Plasma Fibronectin)", Cell 19 pp. 517–525, (1980).

Ueyama et al., "The Role of Factor XIII in Fibroblast Proliferation", Japanese Journal of Experimental Medicine 48 (2), pp. 135–142, (1978).

Bruhn et al., "Effect of the Coagulation and Fibrinolysis Systems on the Wound-Healing Process and Thrombus", Verh. Dtsch. Ges. Inn. Med. 84, pp. 1345–1348, (1978) Chem. Abst. 90:10185v.

*Primary Examiner*—Lionel M. Shapiro
*Assistant Examiner*—John Tarcza
*Attorney, Agent, or Firm*—I. Louis Wolk

[57] ABSTRACT

This invention relates to a novel cell growth-promoting material for use as a supplement to basal tissue culture media for the cultivation of animal cells in vitro and to the method for its preparation. More particularly, it relates to an infusion consisting of growth-promoting material from adult, calf or fetal bovine blood clots as a supplement to basal media for cultivation of animal cells in vitro.

15 Claims, No Drawings

TISSUE CULTURE AND CELL GROWTH-PROMOTING MATERIAL AND ITS METHOD OF MANUFACTURE

BACKGROUND OF THE INVENTION

Over the years, scientists have sought to grow animal cells in completely chemically defined culture media. However, for adequate growth, nearly all types of animal cells require not only a good chemically defined basal medium but, in addition, need a supplement of some naturally occuring biological fluid or tissue extract. These complex supplements have variously consisted of lymph, embryo extract, spinal fluid, skim milk, colostrum, blood plasma or blood serum. Because of its potency, availability and stability, bovine serum, particularly fetal bovine serum has become the most widely used supplement for cell culture. Fetal Bovine Serum known as FBS, is used as a supplement on a large scale in the areas of research, diagnostics, and the production of human and veterinary biologicals. In North America, several large corporations and many smaller companies, in association with the meat packing industry, collectively produce an estimated 150,000 liters of fetal bovine serum per annum. This quantity is produced from not less than about 300,000 liters of whole fetal blood. Thus, in the processing of whole blood to serum, on any scale whatever, the yield of serum is only 45% to 50% by volume of the original whole blood.

Bovine sera are generally produced from carefully drawn and collected whole blood from adult, calf, or fetal animals. Following the natural clotting processes, which may take several hours at 4° C., the serum is separated and the residual clot is discarded, as described for example in U.S. Pat. No. 3,429,867. However, under less stringent bovine blood collection conditions, as when shed blood is taken at the time of slaughter, a quite different kind of clot is formed. In this situation, during exsanguination of the ox carcass, tissue juices from the slashed neck become admixed with the flowing blood and the mixture sets instantly to a rubbery, semi-solid, intractable mass. Such butchering clots are wasted at abattoirs but are an excellent source of growth-promoting materials according to the present invention. Therefore, in what follows, residual bovine blood clots from conventional serum processing as well as butchering bovine blood clots, inclusively, are the starting materials for the present invention.

DESCRIPTION OF THE INVENTION

The applicants have now discovered that the hitherto discarded clot material obtained from the conventional production of bovine blood serum, or clotted whole bovine blood from butchering, may be processed to recover a potent growth-promoting material having superior cell growth-promoting characteristics. The superiority of the growth-promoting material of this invention is evident even by comparison with FBS as a supplement to basal tissue culture media. In addition, the newly discovered material may be used, not only alone as such a supplement but may be combined with FBS thus augmenting the yield from whole fetal blood to a significant extent. It may also be combined with other supplements such as adult bovine serum, calf bovine serum or other supplements.

In addition, the novel supplement referred to may be obtained from adult, calf or fetal bovine clot material separately and combined as desired, or the various types of clots may be combined prior to extraction.

According to the present invention, the treatment of clotted material, either in the case of clotted whole blood or of clots separated from blood following the separation of serum, has been found to permit the recovery of an optimum proportion of the growth-promoting material present in blood, whether adult, calf or fetal. In the case of clotted whole blood wherein the clotting process is allowed to proceed immediately without precautions to delay clotting to separate serum, the present process has been found to recover the growth promoting content of the serum and the clot material in a single procedure. In the case of a process wherein serum is produced separately by separation from clotted blood, it is necessary to carry out the procedure in a manner which will avoid premature clotting to permit separation and recovery of the serum. The separated clots are then treated in accordance with the present invention.

Thus, according to the present invention, there has been discovered a process which permits the recovery from bovine blood clots of 40–50% of the original blood volume of potent growth-promoting material. This additional yield of growth-promoting material consists of 20–25% of volume of the inseparable bovine serum occluded within the clot together with 20–25% by volume of hitherto unused growth-promoting factors present in and intrinsic to the clots. The growth promoting material of the present invention appears to be one or more growth factors (chemical entities promoting attachment, anabolic reactions and mitosis) which act synergistically to promote overall cell proliferation. The growth-promoting material prepared according to the present invention may be used directly as a supplement for cell culture; or it may first be concentrated by well known procedures. The growth-promoting material prepared according to the present invention is a rich source of very highly purified growth factors and purification of the material for use as a cell culture supplement is not necessary.

Operationally in the industry, whole bovine adult or calf blood is collected either from standing herds (donor animals) or from animals for slaughter at selected abattoirs. Whole fetal bovine blood, however, is collected exclusively at abattoirs from the fetuses of healthy gravid cows. Fresh whole blood is withdrawn aseptically into sterile 500 ml or other convenient size, vacutainer blood bottles. The bottles are immediately chilled when the natural clotting process is completed in a few hours. When serum is to be separated first, the sterile clotted blood is centrifuged in the original blood bottles at about 1500 R.P.M. The supernatant serum comprising about 50% by volume of the original whole blood is aspirated from above the certrifuged clot for further processing using well known procedures. The residual bovine blood clots normally discarded in the original blood collection bottles may be the starting material for the present invention.

Alternatively, when bovine serum production is not the primary objective, whole adult or calf blood from slaughtered cattle may be merely collected under sanitary conditions. The resultant butchering clot, from which there is no possibility to prepare serum, is an equally good starting material for the present invention.

It has been discovered that when one volume of sterile physiological saline solution buffered between pH 7.2 to 7.4 is added to one volume of blood clot and the contents are comminuted, mixed, and stored at 4° C. for 24 to 48 hours, a suspension rich in growth-promoting material is produced. That is to say, by the present invention through processes of clot retraction, syneresis, and diffusion into the buffered saline solution, clot occluded blood serum and clot intrinsic growth factors pass into solution. After 24 to 48 hours at 4° C., the infusion may be centrifuged in the original bottle at about 1500 R.P.M., and the supernatant growth-promoting material aspirated off aseptically for further processing. To optimize the yield, the remaining centrifuged, comminuted bovine blood clot may be re-extracted in the same way. The protein content of the supernatant from the first extraction is always about 50% less than the corresponding serum protein content. The supernatants from the first and second extraction, whose protein content may be as low as 75% less than the corresponding serum protein content, may be combined aseptically and stored in the frozen state pending further processing. A third extraction of the clot centrifugate has been attemped but is of no practical value.

Proper comminution of the starting material (bovine blood clots) was found to be of critical importance. Infusion of the intact clot with buffered saline was ineffective. The use of sterile knives, Waring blenders, freeze-thaw cycles etc. released too much hemoglobin from red cells into solution. Linear stainless steel wire drawn through the clot caused the least rupture of red cells with adequate clot disruption. The final method adopted for clot comminution was the use of small stainless steel wire whisks (chef's or kitchen type) fitted into the chuck of a variable speed stirring motor. Immediately following dilution of the blood clot with sterile phosphate buffered saline, the clot may be rapidly comminuted by means of such a sterile wire whisk rotating at low speed with high torque. The use of wire screens is also possible. Thus, it became apparent that sharp-edged cutting devices could not be used and that cutting means having smoothly rounded edges were required.

Various infusion media were also tried. Freshly distilled sterile water caused excessive hemolysis with release of too much hemoglobin. Physiological saline (0.9% sodium chloride) was better, but the most efficient infusion medium was a phosphate buffered saline formulation such as one described by Dulbecco et al; J. Exp. Med. 99, 167, 1954, at a pH from 7 to 9 but preferably pH 7.2 to 7.4. This balanced salt solution may be sterilized by autoclaving or preferably by pressure filtration through an 0.22 micron membrane or cartridge. The sterile phosphate buffered saline solution may be dispensed rapidly from a single large container into the bottles containing the residual centrifuged blood clots. Thorough comminution and mixing is achieved at once, as mentioned above. The bottles are resealed under laminar flow and removed to 4° C. for the infusion period.

Several bottles or several hundred bottles can be prepared for infusion at 4° C. The bottles may be centrifuged at about 1500 R.P.M. in a Beckman model J-6B or International No. 2 Model K centrifuge. Following centrifugation, the supernatant growth-promoting material may be aspirated aseptically into sterile 4 liter serum bottles according to well known procedures. The contents of the 4 liter bottle are mixed and a 50 ml sample withdrawn for the required sublot testing. The remaining approximately 3.5 liters is frozen at −20° C. until sufficient material is accumulated for a master lot (about 100 to 250 liters). The centrifugate may be re-extracted with an equal volume of phosphate buffered saline and the cycle repeated to maximize the yield of growth-promoting material. When hundreds of original infusion bottles are to be centrifuged, the contents of the blood bottles may be transferred aseptically to a sterile (stainless steel) tank and the contents clarified by continuous flow centrifugation. The sterile supernatant is collected in another tank and sampled for testing as before. The bulk pool is stored at −20° C. for final processing while the centrifugate may be re-extracted once more with an equal volume of phosphate buffered saline and the cycle repeated.

For final processing on either moderate or large scale, the procedures are the same. The final pool is mixed, the pH and osmolality checked, and the pool is sequentially pressure clarified through a Seitz type depth filter then directly through a pleated filter membrane such as a Gelman 8.0 to 0.45 micron "Serum" cartridge, and finally through a Pall membrane 0.22 micron cartridge into a sterile receiving tank. Finally, the bulk filled growth-promoting material is sampled for the requisite tests and filled over aseptically in suitable portions in sterile type I glass containers by well known procedures. The final product is an optically clear, red coloured, isotonic, solution with a protein content of approximately 2 to 3% w/v.

In summary, therefore, a preferred process for producing cell growth material from bovine blood clots including fetal bovine blood clots under aseptic conditions comprises:

1. Adding one volume of phosphate buffered saline, pH 7.2 7.4 to one volume of bovine blood clot in the original blood bottle.
2. Mechanical comminution of the clot or coagulum and mixing of the contents.
3. Infusion at 4° C. for 24 to 48 hours.
4. Centrifugation at 1500 R.P.M., 45 minutes.
5. Aspiration of the growth-promoting material (the supernatant fluid).
6. Re-extraction of the centrifugate according to steps 1, 2 and 3 above.
7. Combining the supernatants into suitable sublot pools, storing at −20° C.
8. Testing of samples from sublots.
9. Combining suitable sublots in a final pool, followed by sequential clarification through a Seitz filter than Gelman and Pall membrane or cartridge filter sterilization.
10. The final pool is sampled for the requisite tests and filled over into type I glass containers, and stored at −20° C. until the time of use.

By these means, a growth-promoting material having qualities not obtained by processes described in the literature is achieved. The compositions comprising the unique cell growth-promoting material prepared as described above, and free of extraneous substances, possess potent growth-promoting activity greatly in excess of the homologous serum prepared from the same whole blood or good serum from any commercial source, (based upon equal protein content).

Demonstrations of the uniqueness and effectiveness of the compositions in promoting the growth of various cell types may be shown by the hereinafter described physical, chemical, and cell culture experiments. In the cell growth comparison examples, the new growth-promoting compositions derived from adult, calf and fetal bovine blood clots are presented. Suitable controls using homologous serum from the same original whole blood or our best grade of heterologous fetal bovine serum were used in the same basal medium. Representative cells tested include primary monkey kidney cells, human diploid cell strain WI-38, and the Vero monkey kidney cell line.

Representative nutrient chemically defined basal medium CMRL-1969, Healy et al; Appl. Microbiol., 21; 1, 1971; (CMRL-1969, available from Connaught Laboratories Ltd., Toronto, Ontario.) was used throughout the experiments. It should be noted that the cell growth-promoting material has been coded and sent to participating laboratories to be used in their cell systems. They reported similar results with other cell types and with Eagle's minimum essential medium, Eagle, Science 130; 432, 1959 as the basal medium which can be obtained commercially (e.g. Grand Island Biological Co., Grand Island, N.Y. or K.C. Biological Inc., Lennox, Kan.). Other basal Media as described in the art may also be used, for example, those described in Paul, "Cell and Tissue Culture" 5th ed. (E. and S. Livingstone Ltd., Edinburgh) 1975, Chapter VI and Appendix I.

In the quantitative growth tests performed in our own laboratories and reported here, replicate 25 cm$^2$ Corning tissue culture flasks are prepared each containing 250,000 cells. Culture flasks are prepared in triplicate for each treatment. The treatments are: the addition of basal medium CMRL-1969 (no additives, control); basal medium CMRL-1969+20% clot extract; basal medium CMRL-1969+10% bovine serum. Following seven days incubation at 37° C., the replicate cultures are harvested by well known procedures and the entire population of cells enumerated. The fold increase in cell numbers during 7 days is then calculated. The tables and legends are self explanatory. The following examples illustrate the present invention, but are not to be construed as limiting:

EXAMPLE I

This example relates to the following:
1. A comparison of adult bovine serum and the adult clot extract growth-promoting material (first clot extract) prepared according to the present invention from the same original batch of whole adult bovine blood.
2. The relative growth achieved with these supplements in basal medium CMRL-1969 on primary monkey kidney cells, (epithelial cells).

NOTE: Original volume of whole adult bovine blood 10.5 liters Yield of adult bovine serum 4.9 liters (total protein 6w/v). Yield of growth-promoting material (first clot extract) 5.0 liters (total protein 3.0% w/v). (Second clot extraction not performed).

TABLE I

Average Yield of Primary Monkey Kidney Cells (*Cerocopithecus aethiops*) from Replicate Cultures Grown for 7 days in Basal Medium CMRL-1969 with Adult Bovine Serum and Adult Bovine Clot Extract

| Basal Medium CMRL-1969 By Volume | Supplement Level By Volume | Fold Increase in Cell Population 7 Days |
|---|---|---|
| 90% | Adult Bovine Serum 10% | 8.6× |
| 80% | Adult Bovine Clot Extract 20%* | 27.0× |
| 100% | None Basal Medium Control | 1.4× |

*The volume of the clot extract (3% protein), supplement was adjusted to be equivalent to the whole serum volume (10 ml at 6% protein).

EXAMPLE II

This example relates to the following:
1. A comparison of fetal bovine serum, adult bovine serum, and adult clot extract growth-promoting material (first clot extract) prepared according to the present invention from the same original batch of whole adult bovine blood.
2. The relative growth achieved with these supplements at three different levels in the same basal medium with the human diploid cell strain WI-38 cells, (fibroblast cells).

NOTE:
A=Fetal bovine serum 4.0% total protein
B=Adult bovine serum 7.0% total protein
C=Adult bovine clot extract 3.5% total protein

TABLE 2

Growth of WI-38 Cells in Basal Medium CMRL-1969 alone, and CMRL-1969 with Various Supplements. Replicate cultures were seeded with 2 × 10$^5$ cells/flask (25 cm$^2$) incubated at 37° C. and the cells counted on day 6.

| BASAL CMRL-1969 BY VOLUME | SUPPLEMENT % BY VOLUME | NUMBER OF PASSAGES | FOLD INCREASE OF CELL POPULATIONS |
|---|---|---|---|
| A  98% | 2 | 2 | 4.9× |
|    95% | 5 | 3 | 12.9× |
|    90% | 10 | 3 | 20.2× |
| B  98% | 2 | 3 | 7.8× |
|    95% | 5 | 3 | 11.1× |
|    90% | 10 | 3 | 14.9× |
| C  96% | 4* | 3 | 17.7× |
|    90% | 10* | 3 | 31.5× |
|    80% | 20* | 3 | 36.0× |
|    100% | 0 | 1 | 1.4× |

*Clot extract added at double the serum volumes to compensate for its lower protein content. (20 ml clot extract at 3.5% protein = 10 ml adult serum at 7% protein.

EXAMPLE III

This example relates to the following:
1. A comparison of a leading commercial fetal bovine serum, A; fetal bovine serum, B; fetal bovine clot extract, C. Supplements B and C were prepared in the inventor's laboratory according to the present invention from the same original whole fetal bovine blood.
2. The relative growth achieved with these 3 supplements at the same level in basal medium CMRL-1969.

NOTE:
A—fetal bovine serum 3.9% total protein
B—fetal bovine serum 4.3% total protein
C—invention fetal clot extract 2.1% total protein

TABLE 3

Growth of WI-38 Cells in Basal Medium CMRL-1969 alone. supplemented with: Commercial Fetal Bovine Serum, Dextran Products Ltd. Fetal Bovine Serum and Homologous Fetal Bovine Clot Extract, Replicate cultures seeded with 2 × 10$^5$ cells/flash (25 cm$^2$), incubated at 37° C., and the cells enumerated on day 7. Single passage.

| BASAL CMRL-1969 BY VOLUME | SUPPLEMENT | FOLD INCREASE IN CELL POPULATION 7 DAYS |
|---|---|---|
| A | 90% | Fetal Bovine Serum 10% | 8× |
| B | 90% | Fetal Bovine Serum 10% | 14× |
| C | 80% | Fetal Bovine Clot Extract 20%* | 29× |

TABLE 3-continued

Growth of WI-38 Cells in Basal Medium CMRL-1969 alone, supplemented with: Commercial Fetal Bovine Serum, Dextran Products Ltd. Fetal Bovine Serum and Homologous Fetal Bovine Clot Extract, Replicate cultures seeded with $2 \times 10^5$ cells/flask (25 cm$^2$), incubated at 37° C., and the cells enumerated on day 7. Single passage.

| BASAL CMRL-1969 BY VOLUME | SUPPLEMENT | FOLD INCREASE IN CELL POPULATION 7 DAYS |
|---|---|---|
| 100% | None (control) | 1.3× |

*The volume of the clot extract (2% protein) Supplement was adjusted to be equivalent in protein content to the fetal bovine serum volume (10 ml at 4% protein).

EXAMPLE IV

This example relates to the following:

1. Whole fetal bovine blood (19 liters) from which fetal bovine serum was prepared by conventional methods and the growth-promoting material (first clot extract) was prepared from the residual clots according to the present invention. In this example, the centrifugate from the first clot extraction was re-extracted according to the present invention to produce the growth-promoting material (second clot extract) in order to maximize the yield.

2. The relative growth achieved with these supplements in basal medium CMRL-1969 on the African Green Monkey kidney continuous cell line Vero, (epithelial cells).

NOTE: Original Volume of whole fetal bovine blood 19 liters. Yield of fetal bovine serum 9 liters, (total protein 4% w/v). Yield of growth-promoting material (first clot extract) 10 liters (total protein 1.9% w/v). Yield of growth-promoting material (second clot extract) 10 liters (total protein 0.9% w/v).

TABLE 4

Growth of Vero Cells in Basal Medium CMRL-1969 Alone, Supplemented with Dextran Products, Ltd. Fetal Bovine Serum, Homologous First Fetal Bovine Clot Extract and Homologous Second Fetal Bovine Clot Extract. Replicate Cultures seeded with $2 \times 10^5$ cells/flask (25 cm$^2$), incubated at 37° C. and the cell populations enumerated on day 7.

| BASAL MEDIUM CMRL-1969 BY VOLUME | SUPPLEMENT LEVEL BY VOLUME | FOLD INCREASE IN CELL POPULATION 7 DAYS |
|---|---|---|
| 90% | Fetal Bovine Serum 10% (Source B) | 12× |
| 80%* | Invention - First Clot Extract 20% | 16× |
| 60% | Invention Second Clot Extract 40% | 15× |
| 100% | 0 (Control) | 1.5× |

*Volume of clot extract (2% protein) adjusted to be equivalent in protein content to the FBS (10 ml at 4% protein)

EXAMPLE V

This example relates to the following:

1. Whole bovine calf blood was collected at an approved abattoir under sanitary conditions from calves at slaughter. The resultant butchering clots, approximately 2 liters each contained in sterile 4½ liter wide mouth bottles were removed to the laboratory. The firm clots were dispersed in equal volume of phosphate buffered saline, according to the present invention, without the preliminary separation of the calf serum. The centrifugate from the first butchering clot extract was re-extracted according to the present invention to produce a second butchering clot extract.

2. The relative growth achieved with these supplement in basal medium CMRL-1969 on the African Green Monkey kidney continuous cell line Vero (epithelial cells).

NOTE: Original volume of fresh clotted whole calf blood 20 liters. Yield of calf serum 0 liters.

Yield of growth-promoting material (first clot extract) 10 liters, (total protein 2.5% w/v). Yield of growth-promoting material (second clot extract) 8.5 liters, (total protein 1.8% w/v).

TABLE 5

Growth of Vero cells in basal medium CMRL-1969 alone, supplemented with Dextran Products Limited's fetal bovine serum, supplemented with the first clot extract, and supplemented with the second clot extract. Replicate cultures seeded with $2 \times 10^5$ cells/flask (25 cm$^2$), incubated at 37° C. and the cell populations enumerated on day 7.

| Basal Medium CMRL-1969 By Volume | Supplement Level By Volume | Fold Increase in Cell Population 7 Days |
|---|---|---|
| 84% | Invention - First Clot Extract 16% | 25× |
| 78% | Invention - Second Clot Extract 22% | 37× |
| 90% | Fetal Bovine Serum 10% | 20× |
| 100% | 0 (Control) | 1.5× |

In this example, the relative growth of the Vero cells, or the cell yields showed the following data:

| MEDIUM | POPULATION INITIAL (I) | POPULATION FINAL (F) | FOLD INC. F/I = | DOUBLING TIME HOURS |
|---|---|---|---|---|
| Ext. #2 | $2 \times 10^5$ | $7.5 \times 10^6$ | 37× | 12 |
| Ext. #1 | $2 \times 10^5$ | $5 \times 10^6$ | 25× | 12 |
| FBS | $2 \times 10^5$ | $4 \times 10^6$ | 20× | 15.5 |

As the data illustrates, it is possible to achieve maximum cell yields—nearly twice the number of cells with extract #2 as with top grade fetal bovine serum, and 48 hours sooner. In order to make a viral vaccine commercially, a manufacturer should be able to obtain at least 10 population doublings during three successive subcultivations of his cells, over 3 weeks, or a 7 day cycle. With extract #2, this could be achieved in 13 days (4 doublings/5 days + 4 doublings/5 days + 2 doublings/3 days).

As the foregoing examples illustrate, the clot extracts demonstrate a high degree of cell growth by comparison with the controls and adult serum or FBS.

In Example I, Table 1, the high degree of growth-promoting activity of adult clot extract by comparison with adult bovine serum is clearly demonstrated with primary monkey kidney cells.

In Example II, Table 2, the adult bovine clot extract shows a high degree of growth-promoting activity with human deploid cells compared to both adult and fetal bovine serum.

In Example III, Table 3, significantly greater growth-response with human diploid cells is obvious from the first extract of the bovine fetal clot material compared with the control and with two samples of fetal bovine serum from different sources.

Example IV, Table 4, shows the superior activity of the first and second fetal clot extracts over fetal bovine serum extracted from the same sample of whole fetal blood, with African Green Monkey kidney cells.

Example V, Table 5, shows the superior growth activity of first and second butchering clot extracts over fetal bovine serum as supplements (same protein contents) to basal medium CMRL-1969. This example illustrates that when required, potent clot extracts can be prepared from freshly clotted abattoir blood without the intermediate production of bovine serum.

Summarizing the procedures and examples, the raw material for the production of bovine serum for cell culture purposes is normal whole blood taken without anticoagulants or other additives. Following the natural clotting process and the aseptic removal of the supernatant serum (50% by volume), the residue, (50% by volume), consists of about 1/5 by volume entrained serum, and 4/5 coagulum or clot. These relationships obtain for fetal, calf and adult bovine blood clot residues. The infusions of the clot residues, following clarification by filtration or centrifugation consist of a phosphate buffered balanced salt solution containing 20% occluded bovine serum from the clot and 80% complex clot components which in the present invention are called growth-promoting material or briefly "clot extract." From dose response data, it is calculated that the overall growth-promoting activities of the classes of ingredients in the culture medium are as described in the above examples are as follows:

| | | |
|---|---|---|
| 1. | Basal Medium CMRL-1969 | 1.4× |
| 2. | Residual 4 to 5 ml adult or fetal bovine serum in the extract | 11.1× |
| 3. | Active principles in the actual clot extract | 23.5× |
| | TOTAL | 36.0× |

Or, put in another way, the relative growth responses shown by the examples are: basal medium CMRL-1969 4%, adult or fetal bovine serum 31%, intrinsic adult or fetal bovine clot factors 65%. Of course, with other basal media, cells, and conditions, the proportions would vary but the same type of increase in growth-promotion would be shown by the applicant's product.

From many dialysis and Sephadex exclusion chromatography experiments, we can state categorically that none of the biological activities reside in the low molecular weight fractions of clot extract but remain with the macromolecules.

That the composition of the growth-promoting material (clot extract) differs from whole serum is readily shown by zonal electrophoresis of adult or fetal bovine serum, adult or fetal bovine clot extracts in the same agarose gel. Clot extracts are characterized by a prominent electrophoretic pre-beta band which is unique and is a reliable "marker" for clot extracts.

Although either of the adult, calf or fetal bovine clot extracts may be utilized separately, they may also be combined with each other in any desired proportion, or they may be combined with adult, calf or fetal bovine sera or with other supplements.

We claim:

1. A process for the production of a growth promoting supplement for tissue culture media providing improved cell and tissue growth which comprises comminuting bovine blood clot with cutting means having smoothly rounded edges to minimize disruption of red blood cells in the presence of a buffered aqueous saline solution to form a suspension of comminuted blood clot in said saline solution, allowing the resulting suspension to become thoroughly infused to allow clot occluded blood serum and clot intrinsic blood factors to pass into said saline solution, and separating said saline solution containing said growth promoting material from said suspension to provide said growth promoting supplement in saline solution.

2. A process according to claim 1 wherein residue remaining after separation of the said solution of growth promoting material is reextracted and infused in suspension with a further quantity of buffered aqueous saline solution, and the infused solution separated from said last named suspension to provide an additional fraction of growth promoting material in saline solution.

3. A process according to claim 1 wherein the said bovine blood clots are produced by clotting whole bovine blood and separating serum therefrom prior to comminuting said blood clots.

4. A process according to claim 1 wherein the blood clots are present in whole clotted bovine blood which comprises said clots and serum which is present during comminution of said clots whereby substantially all of the serum including that which has been occluded by the clots is dissolved into said saline solution along with clot intrinsic blood factors.

5. A supplement for cell and tissue growth produced by the method of claim 4.

6. A process according to claim wherein the said bovine blood clots are formed from adult bovine blood.

7. A supplement for cell and tissue growth produced by the method of claim 6.

8. A process according to claim 1 wherein the said bovine blood clots are formed from calf blood.

9. A process according to claim 1 wherein the said bovine blood clots are butchering clots produced during exsanguination of bovine carcasses after slaughter.

10. A process according to claim 1 wherein the said blood clots are formed from fetal calf blood.

11. A composition for the culture of animal cells in vitro which comprises a tissue culture medium in combination with a sufficient proportion of a growth promoting supplement produced by the method of claim 1 to provide an improved rate of cell growth.

12. A growth promoting supplement for tissue culture media providing improved cell and tissue growth produced by the method of claim 1.

13. A method for the culture of animal cells which comprises admixing a tissue culture medium for the growth of said cells with a cell growth supplement produced by the method of claim 1, in sufficient proportion to provide an improved rate of cell growth, and incubating said animal cells therein.

14. A process for the production of a growth promoting supplement for tissue culture media providing improved cell and tissue growth which comprises comminuting bovine blood clots while minimizing disruption of red blood cells and liberation of hemoglobin therefrom in the presence of phosphate buffered saline solution at a pH of 7.2 to 7.4 to form a suspension of said comminuted clot in said saline solution, allowing said suspension to become thoroughly infused at a temperature of about 40° C. for 24 to 48 hours to allow occluded blood serum and clot intrinsic blood factors to pass into said saline solution, centrifuging the resulting suspension to separate suspended solids from said solution, and recovering said saline solution as said growth promoting supplement containing said occluded blood serum and said clot intrinsic factors.

15. A growth promoting supplement for basal tissue culture media produced by the method of claim 14.

* * * * *

UNITED STATES PATENT AND TRADEMARK OFFICE
CERTIFICATE OF CORRECTION

PATENT NO. : 4,520,107
DATED : May 28, 1985
INVENTOR(S) : George M. Healy and Kenneth D. Curry It is certified that error appears in the above-identified patent and that said Letters Patent are hereby corrected as shown below:

In [75] Inventors: "George M. Healy, Scarborough; Kenneth D. Curry, Toronto, both of Canada"

should read --George M. Healy, Scarborough; Kenneth D. Curry, Toronto; Hildegarde M. G. Macmorine, Ontario; Folke Holst, Ontario, all of Canada--

Signed and Sealed this

Twelfth Day of November 1985

[SEAL]

Attest:

DONALD J. QUIGG

Attesting Officer

Commissioner of Patents and Trademarks